(12) United States Patent
Carson et al.

(10) Patent No.: US 6,270,780 B1
(45) Date of Patent: Aug. 7, 2001

(54) COSMETIC COMPOSITIONS CONTAINING RESVERATROL

(75) Inventors: Robert George Carson, Rahway; Krupa Patel, Edison; Marieann Carlomusto, Palisades Park; Carol Annette Bosko, Oradell; Sreekumar Pillai, Wayne; Uma Santhanam, Tenafly; Ronni Lynn Weinkauf, River Edge; Koichi Iwata, Ridgefield Park; Laura Rose Palanker, Jackson, all of NJ (US)

(73) Assignee: Chesebrough-Pond's USA Co., division of Conopco, Greenwich, CT (US)

( * ) Notice: Subject to any disclaimer, the term of this patent is extended or adjusted under 35 U.S.C. 154(b) by 0 days.

(21) Appl. No.: 09/098,121

(22) Filed: Jun. 16, 1998

Related U.S. Application Data

(63) Continuation-in-part of application No. 08/900,795, filed on Jul. 25, 1997.

(51) Int. Cl.[7] .............................. A61K 6/00; A61K 7/00
(52) U.S. Cl. ........................ 424/401; 514/844; 514/846
(58) Field of Search ........................... 424/401; 514/844, 514/846

(56) References Cited

U.S. PATENT DOCUMENTS

| | | | |
|---|---|---|---|
| 4,438,095 | 3/1984 | Grollier | 424/70 |
| 5,034,226 | 7/1991 | Beck | 434/196.1 |
| 5,171,577 | 12/1992 | Griat | 424/450 |
| 5,391,724 | 2/1995 | Kindl | 536/23.2 |
| 5,439,672 | 8/1995 | Zabotto | 424/59 |
| 5,683,683 | 11/1997 | Scafidi | 424/70.19 |
| 5,690,947 | * 11/1997 | Habif et al. | 424/401 |

FOREIGN PATENT DOCUMENTS

| | | |
|---|---|---|
| 64-038009 | * 2/1989 | (JP) . |
| 8-175960 | * 7/1996 | (JP) . |
| 9-328410 | 12/1997 | (JP) . |
| 10-045566 | 2/1998 | (JP) . |

OTHER PUBLICATIONS

Abstract of Medical Science Research 26:(4)235–237, Apr. 1998.

Creidi et al., Effect Of A Conjugated Oestrogen Cream, Premarin®On Aging Facial Skin, Maturitas, 19 p. 211–23, 1994.

Knight et al., Phytoestrogens—A Short Review, Maturitas, 22: 167–75, 1995.

Jang et al., Cancer Chemopreventive Activity Of Resveratrol, A Natural Product Derived From Grapes Science 275: 218–220, 1997.

M.A. Puleo, Fennel And Anise As Estrogenic Agents Journal of Ethnopharmacology, 2(1980)337–344.

Derwent abstract of JP application 6336423 dated Dec. 6, 1994.

Derwent abstract of JP application 6336422 dated Dec. 6, 1994.

Derwent abstract of JP application 6336419 dated Dec. 6, 1994.

Derwent abstract of JP application 6336421 dated Dec. 6, 1994.

Am. Enol. Vric., vol. 47, No. 1, 1996.

Gehm et al., Resveratrol, a polyphenolic compound found in grapes and wine, is an agonist for the estrogen receptor Proc. Natl. Acad. Sci. USA, vol. 94, pp 14138–14143, Dec. 1997.

International Search Report in the application of PCT/EP98/04223.

Patent Abstracts of Japan, abstract of Japanese patent application 10 045566; Feb. 17, 1998.

Patent Abstracts of Japan, abstract of Japanese patent application 09 328410; Dec. 22, 1997.

CA 120645 abstract of Japanese patent application 01038009; Feb. 8, 1989.

Embase 95287548, abstract of "Vitis Vinifera L." by Bombardelli et al. in Fitoterapia, 1995, 66/4 (291–317) and full text of article.

Kang et al., Inhibitory effects of α–viniferin and resveratrol on the L–dopa oxidase activity of tyrosinase, Medical Science Research 26, p. 235–237, 1998.

Colowick and Kaplan Methods in Enzymology vol. 1, p. 140, 1956.*

* cited by examiner

*Primary Examiner*—Thurman K. Page
*Assistant Examiner*—Todd D Ware
(74) *Attorney, Agent, or Firm*—Milton L. Honig; Rimma Mitelman

(57) ABSTRACT

Resveratrol, a component of a variety of common edible plants, including peanuts and red grapes, is a phytoestrogen. Resveratrol inhibits proliferation of skin epidermal cells (keratinocytes) and stimulates their differentiation. Resveratrol was also found to inhibit melanin production by skin cells and to alleviate skin irritation that may be caused by alpha-hydroxy acids. Resveratrol is useful in improving the appearance of wrinkled, lined, dry, flaky, aged or photodamaged skin and improving skin thickness, elasticity, flexibility, radiance, glow and plumpness.

1 Claim, No Drawings

COSMETIC COMPOSITIONS CONTAINING RESVERATROL

This is a continuation-in-part of application Ser. No. 08/900,795, filed on Jul. 25, 1997.

FIELD OF THE INVENTION

Cosmetic compositions containing resveratrol, a natural estrogen derived from plants, and methods of conditioning skin by applying such compositions to the skin.

BACKGROUND OF THE INVENTION

The human skin consists of two major layers, the bottom thicker layer, dermis and the top thinner layer the epidermis. Dermis is the layer which provides the strength, elasticity and the thickness to the skin. With aging, the thickness of the dermal layer is reduced and this is believed to be partially responsible for the formation of wrinkles in aging skin. The top layer of human skin or the epidermis which provides the resilience and the barrier properties of the skin, is composed of many different cell types. Keratinocytes are the major cell type of the epidermis (75–80% of the total number of cells in the human epidermis). Within the epidermis the keratinocytes reside in four distinct stages of differentiation. Epidermal differentiation is important for providing the essential function of the skin, namely to provide a protective barrier against the outside environment and to prevent loss of water from the body. Formation of the cornified envelope is the final stage of keratinocyte differentiation. The enzyme responsible for the formation of cornified envelopes, trans-glutaminase is a marker of epidermal differentiation. Agents which increase the thickness of the dermal layer and increase the differentiation of keratinocytes in the epidermal layer should therefore be ideal compounds for providing skin conditioning and anti-aging benefits.

Estrogens and synthetic compounds which act like estrogens are known to increase the thickness of the dermal layer and reduce wrinkle formation in the aging skin. Changes in the skin such as skin dryness, loss of skin elasticity and plumpness occurring after menopause are attributed to the lack of estrogen production. Estrogen therapy prevents or slows down many of the changes associated with aging skin (Creidi et al., Effect of a conjugated oestrogen cream (Premarin®) on aging facial skin, Maturitas, 19, p.211–23, 1994). A synthetic estrogen, diethyl stilbestrol, has the following structure:

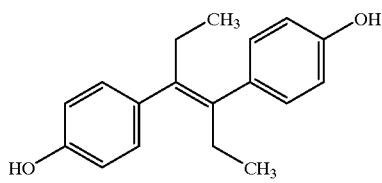

This structure is very different from the structure of natural estrogen, estradiol:

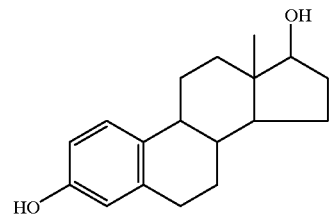

In recent years, phytoestrogens (i.e., natural compounds which have estrogen-like activity and which are found in plants) have been increasingly used for therapeutic purposes. Some of the uses described are as hypocholesterolemic and antiatherogenic agents, treatment of cardiovascular diseases especially in postmenopausal women, treatment for osteoporosis in the elderly and as an anticancer agent especially against breast cancer, endometrial and cervical cancer in women (Knight et al., Phytoestrogens—a short review, Maturitas, 22: 167–75, 1995).

The consumer demand for "natural" based products has been growing in recent years. The consumers perceive chemical synthesis as environmentally unsafe. A chemically synthesized ingredient may contain harsh chemicals. Natural products are perceived as pure and mild and superior to chemically synthesized products. However, delivering a cosmetic benefit from plant sources is not trivial. In order to derive a real benefit from a "natural" source a specific active in the plant has to be identified which truly delivers a cosmetic benefit.

One known phytoestrogen is photoanethole:

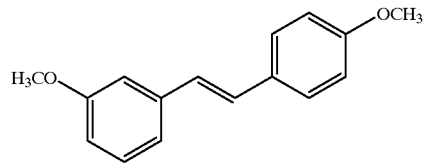

Photoanethole has not been described for topical or cosmetic use.

The present invention is based at least in part on the discoveries that resveratrol is a phytoestrogen, that it inhibits keratinocyte proliferation, increases keratinocyte differentiation, inhibits melanin production by the skin cells, and alleviates irritation or sting potentially associated with the use of alpha-hydroxy acids.

Resveratrol is a compound found in a variety of plants. Isolation and characterization of resveratrol have been described from a variety of plants such as the roots of Japanese knotweed (Powell et al., Phytochemistry 35, p.335, 1994), from wine and grapes (Goldberg et al; J. Agric. Food Chem., 43, p.1820, 1995 and Cellotti et al., "Resveratrol content of some wines obtained from dried Valpolicella grapes: Recioto and Amarone., J chromatogr A (Netherlands) 730: 47–52,1996), and from peanut plant cultures (Kindl et al., U.S. Pat. No. 5,391,724). Red grapes and red wine contain high amounts of resveratrol and this compound is claimed as one of the reasons for cardiovascular health in wine drinkers. In addition, resveratrol has been shown to be a potent cancer chemopreventive agent and an anti-inflammatory agent. Resveratrol has also been reported to induce differentiation of human promyelocytic leukemia cells (Jang et al., Cancer chemopreventive activity of resveratrol, a natural product derived from grapes, Science 275: 218–220, 1997). Jang et al describe resveratrol's use as an anticancer agent against carcinogen-treated mouse skin cells in culture.

Cosmetic compositions containing grape extract have been described. See for instance abstract of Japanese patent application 06336421 ("JP '421"), disclosing the use of 0.5% grape extract in cosmetic compositions. Scafildi et al. (U.S. Pat. No. 5,683,683) and Zabotto et al. (U.S. Pat. No. 5,439,672) disclose cosmetic compositions containing grape seed oil. Griat et al. (U.S. Pat. No. 5,171,577) disclose cosmetic foams containing cosmetic pips. None of these disclosures, except JP '421, mentions any amount of the grape to be used. JP '421 teaches the presence of 0.5% of grape extract. According to Agricultural Research Service of the United States Department of Agriculture, resveratrol concentration in whole berries is about 15 ppm. Then, the resveratrol concentration in 0.5% grape seed extract is 0.33 micromolar or 0.0000075 wt. %.

The art discussed above does not describe the use of resveratrol for skin care or cosmetic use, does not teach that resveratrol is a phytoestrogen, or that it inhibits keratinocyte proliferation, or that it promotes differentiation of keratinocytes, or that it affects melanin production by the skin cells, or that it controls skin irritation caused by alpha-hydroxy acids.

SUMMARY OF THE INVENTION

The present invention includes skin care composition comprising resveratrol in an amount of from 0.00002 to 10 wt. % and a cosmetically acceptable vehicle.

The present invention also includes a method of improving or preventing the condition of wrinkled, lined, dry, flaky, aged or photodamaged skin and improving skin thickness, elasticity, flexibility, radiance, glow and plumpness, which method includes applying to the skin the inventive composition. Compositions of the invention are intended for topical application to mammalian skin which is already dry, flaky, lined, wrinkled, aged, photodamaged, or the inventive compositions may be applied prophylactically to normal healthy skin to prevent or reduce the deteriorative changes. Inventive compositions may also be used for treatment of skin hyperproliferation disorders, such as psoriasis or winter xerosis.

The present invention also includes cosmetic methods of delivering estrogenic activity to the skin, inhibiting keratinocyte proliferation in human skin and increasing keratinocyte differentiation. The present invention also includes a cosmetic method of lightening the skin color. The invention further includes a cosmetic method of controlling skin irritation, sting or inflammation which may be caused by alpha-hydroxy acids. In this respect, the invention also includes cosmetic composition containing resveratrol in combination with an alpha-hydroxy acid.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the composition, unless otherwise specified.

Resveratrol (also known as 5-parahydroxystyryl resorcinol, or 3,4'5-stilbenetriol) is an essential ingredient of the inventive composition. Resveratrol has the following structure:

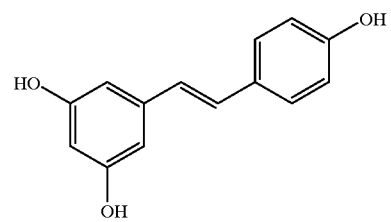

Resveratrol may be obtained commercially from Sigma.

In general, the amount of resveratrol in the inventive compositions is in the range of from 0.00002 to 10% by weight composition. Preferably in order to lower cost and maximize the effect the amount of resveratrol is in the range of from 0.001% to 5% and most preferably is in the range of from 0.1% to 5%.

The composition according to the invention also comprises a cosmetically acceptable vehicle to act as a diluant, dispersant or carrier for resveratrol in the composition, so as to facilitate its distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 mm²/s (centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, water comprises at least 50 wt. % of the inventive composition, most preferably from 60 to 80 wt. %, by weight of the composition.

In one embodiment of the invention, the inventive compositions also include an alpha-hydroxy acid.

Hydroxyacids enhance proliferation and increase ceramide biosynthesis in keratinocytes, increase epidermal thickness, and increase desquamation of normal skin resulting in smoother, younger looking skin.

The hydroxy acid can be chosen from alpha-hydroxy acids, beta-hydroxyacids (e.g. salicylic acid), other hydroxycarboxylic acids (e.g., dihydroxycarboxylic acid, hydroxydicarboxylic, hydroxytricarboxylic) and mixtures thereof or combination of their stereoisomers (DL, D or L).

Most preferred inventive compositions containing resveratrol anti-irritant include glycolic acid and/or lactic acid because these ingredients have been found to have potential to cause irritation yet they were found to be particularly efficacious at delivering cosmetic benefits.

Preferably the hydroxy acid is chosen from alpha-hydroxy acids having the general structure (1)

(1)

where M is H or a saturated or an unsaturated, straight or branched hydrocarbon chain containing from 1 to 27 carbon atoms.

Even more preferably the hydroxy acid is chosen from lactic acid, 2-hydroxyoctanoic acid, hydroxylauric acid, glycolic acid, and mixtures thereof. When stereo isomers exist, L-isomer is most preferred.

A particular advantage of the inventive compositions is that higher amounts of hydroxy acids may be employed without causing skin irritation. Preferably the amount of the hydroxy acid component present in the composition according to the invention is from 0.01 to 20%, more preferably from 2 to 12% and most preferably from 4 to 12% by weight.

It is to be understood that depending on the pH of the composition, the hydroxy acid may be present as a salt, e.g. ammonium or potassium or sodium salt.

Although the inventive compositions may have any pH in the general range of 2.5 to 10, the inventive compositions are particularly useful when they are at an acidic pH (especially if they contain a hydroxy acid), preferably 3–5 and most preferably at a pH of 3–4, because such compositions are particularly irritating.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

The inventive compositions preferably include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Emollients are often incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Use of the Composition

The composition according to the invention is intended primarily as a product for topical application to human skin, especially as an agent for conditioning, moisturizing and smoothening the skin, and preventing or reducing the appearance of lined, wrinkled or aged skin.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507, incorporated by reference herein. The invention accordingly also provides a closed container containing a cosmetically acceptable composition as herein defined.

The following specific examples further illustrate the invention, but the invention is not limited thereto. In all examples, resveratrol was obtained from Sigma. Student t-test was used to calculate all p-values.

EXAMPLE 1

This example illustrates that resveratrol is a phytoestrogen.

The following test was employed to determine whether resveratrol has an estrogen-like activity:

The ZR75 cell line is a ductal breast carcinoma cell line, originally isolated from malignant mammary epithelium of a sixty-three year old Caucasian female (Engel et al., Human breast carcinoma cells in continuous culture: A review., Cancer Res., 38: 4327–4339, 1978). This cell line contains receptors for estrogen, progesterone and other steroid hormones, but responds through an increase in proliferation only to estrogen. The cell line contains high affinity estrogen-specific receptors. Therefore, this cell line is used for testing estrogen-like activity (Markiewicz et al., In vitro bioassays of non-steroidal phytoestrogens, J. Steroid Biochem. Molec. Biol., 45: 399–405, 1993)

Methodology Used for Determining the Rate of DNA Synthesis in Cells

The incorporation of $^3$H-thymidine by cultured cells was used as an assay of cell proliferation (both for ZR75 cells and for keratinocytes). Thymidine is one of four deoxynucleosides which are the monomeric units of DNA. Prior to cell division of a somatic cell, the complete genome of the cell undergoing cell division is replicated. This involves large scale DNA synthesis by the cell and enables both daughter cells to receive identical copies of the genetic material. When $^3$H-thymidine is included in the culture media of cells which are synthesizing DNA in preparation for cell division then the labeled thymidine is incorporated into the newly synthesized DNA. The extent of incorporation of $^3$H-thymidine into a population of cells is proportional to the rate of DNA synthesis by this population of cells and therefore an indication of their cellular proliferation.

ZR75 cells (from American Type Culture Collection, Rockville, Md.) were grown in RPMI1640 media (from Gibco Life Technologies) with 10% fetal bovine serum (FBS), 100 units penicillin per ml and 100 units of streptomycin per ml. All incubations were performed at 37° C. in 5% $CO_2$. The media did not contain Phenol Red (a weak estrogen mimetic). The cells were seeded at a density of one million per 75 cm2 flask. For the experiment, the cells were seeded in 24 well plates at 100,000 cells per ml per well.

After growing for 24 hours, the media was removed, the cells were washed with PBS (phosphate buffered saline, 0.01 M sodium phosphate, 0.138 M sodium chloride, 0.0027 M potassium chloride, pH 7.4) and 1 ml of RPMI 1640 without serum (but with streptomycin and penicillin) was added. Stock solutions of resveratrol in dimethyl sulfoxide (DMSO) and estradiol in water were prepared. Various concentrations of resveratrol and estradiol, as indicated in Table 1, were then dosed directly into each well. After another 24 hours, one $\mu$Ci of [methyl-3H] thymidine was added to each well. The media was removed after 24 hours. The cells were washed once in PBS, the PBS was removed completely and the cells were left on ice to incubate with 1 ml per well of 10% TCA (trichloroacetic acid) for 30 minutes. The plates were washed 3 times with 5% TCA to remove all traces of thymidine which wasn't incorporated into the cells. 500 $\mu$l of 0.1M sodium hydroxide was added to each well and the plates were incubated at room temperature for at least 30 minutes. 250 $\mu$l of each sample was transferred to scintillation vials and after adding 5 mL of counting fluid, the vials were counted for 5 minutes each on a setting for tritium. Data from quadruplicate wells were calculated as % thymidine incorporation into DNA compared to that of control wells which did not receive any resveratrol or estradiol. Values were expressed as mean of quadruplicate wells +/− standard deviation.

The results that were obtained are summarized in Table 1

TABLE 1

| Compound ($\mu$M) | EXPT 1 DNA synthesis. (% of Control) | EXPT 1 p value | EXPT 2 DNA synthesis Control) | EXPT 2 p value |
|---|---|---|---|---|
| Control (water) | 100 ± 20.4 | — | 100 ± 1.9 | — |
| Estradiol (1 nM) | 220 ± 11 | 0.00059 | 133.4 ± 29 | 0.062 |
| 10 nM | 210 ± 9.7 | 0.00079 | 152 ± 17.7 | 0.0011 |
| 100 nM | 205 ± 15.6 | 0.0016 | 156 ± 11.7 | 0.00008 |
| 1000 nM | 190 ± 24.5 | 0.0068 | 142 ± 18.3 | 0.0039 |
| Control (DMSO) | 100 ± 7.0 | — | 100 ± .08 | — |
| Resveratrol (0.5 $\mu$M) | 69.7 ± 10.0 | | 56.8 ± 4.2 | |
| 1 $\mu$M | 58.8 ± 9.0 | | 60.5 ± 3.6 | |
| 5 $\mu$M | | | 158.8 ± 4.1 | 0.000008 |
| 10 $\mu$M | 207.8 ± 32.5 | 0.0026 | 163 ± 13.7 | 0.00029 |
| 15 $\mu$M | | | 119 ± 2.5 | 0.00009 |
| 20 $\mu$M | 134.8 ± 21.4 | 0.612 | 68 ± 3.9 | |
| 40 $\mu$M | 60.8 ± 26.4 | | | |
| 50 $\mu$M | 4.1 ± 1.4 | | | |

The control $^3$H thymidine incorporation value for experiment 1 was 71513 cpm and the control for experiment 2 was 114958 cpm.

The results in Table 1 demonstrate that estradiol, a known estrogen, stimulated proliferation of ZR 75 cells, as expected. Resveratrol increased proliferation of ZR 75 cells at a concentration from 5 to 20 $\mu$M.

EXAMPLE 2

This example demonstrates that resveratrol inhibits proliferation of keratinocytes.

1. Normal human keratinocytes isolated from neonatal foreskins by trypsin treatment were grown in Dulbecco's modified Eagle's medium (DME)/5% fetal calf serum in the presence of mitomycin C treated 3T3 mouse fibroblasts for establishing dividing keratinocyte colonies. Keratinocytes were grown under the above condition until their third passage.
2. For the experiments, third passage keratinocytes were plated into a serum-free keratinocyte growth medium (KGM; obtained from Clonetics, San Diego, Calif.) containing 0.09 mM calcium. About 30,000 cells were plated into each well of 6 well cell culture plates and grown for 5 days, until the cells reach about 40% confluence.
3. Medium was changed to fresh medium (KBM; obtained from Clonetics) and resveratrol at various concentrations as indicated in Table 2 was added to the medium from a DMSO (Dimethylsulfoxide) stock solution. The final DMSO concentration in the cultures was 0.1%. Control cultures received no resveratrol but were dosed with 0.1% DMSO. Each concentration was tested in three separate wells. After four hours, 1 $\mu$Ci of $^3$H-thymidine (Amersham Corp., Sp activity 40 Ci/mmol) was added to 1 ml of medium in each well. The cells were incubated for 2 hours. The amount of $^3$H-thymidine associated with the cellular DNA of keratinocytes was assessed as described below.

4. The medium was aspirated, and the wells washed with 1 ml PBS. The DNA and proteins of the cells in the plate were then precipitated by adding 1 ml of ice-cold 10% TCA. The plates were left on ice for 30 minutes to complete the precipitation process. TCA was then aspirated and each well was then washed 4 times with 5% TCA. The cells in the wells were dissolved in 0.5 ml of 1.0N sodium hydroxide. 200 $\mu$l was then transferred to a scintillation vial for assessing thymidine incorporation and 25 $\mu$l was used for a protein assay using BCA protein assay reagent as described below. 5 ml of a scintillation fluid (Scintiverse) was added to the rest of the solution in the vial, and the vials were counted in a scintillation counter to determine the amount of radioactivity in each vial.

BCA (Bicinchoninic Acid)—Protein Assay

25 $\mu$l of cell suspension were placed in a 96 well plate. Standards of BSA (bovine serum albumin) in 0.1N Sodium Hydroxide were also pipetted in triplicate in the same 96 well plate. Pierce BCA protein assay reagent was added (200 $\mu$l/well) and plate was incubated for 2 hours at room temperature. Absorbance was read at a wavelength of 570 nm on a Dynatech MR7000 plate reader.

The DNA synthesis rate was then calculated as cpm $^3$H-thymidine incorporated into total cellular DNA/$\mu$g of cell protein for each individual well. Mean and standard deviation for each group were also calculated. These numbers were also expressed as percent of control wells. Each data point is expressed as mean of triplicate wells±standard deviation.

The results that were obtained are summarized in Table 2. p values of less than 0.5 were considered to indicate statistical significance.

TABLE 2

| Resveratrol ($\mu$M) | DNA synthesis (cpm/$\mu$g protein) | % inhibition | P value |
| --- | --- | --- | --- |
| Experiment 1 | | | |
| 0 | 29.52 ± 4.44 | 0 | — |
| 50 | 0.62 ± 0.09 | 98 | 0.012 |
| Experiment 2 | | | |
| 0 | 17.17 ± 1.21 | 0 | — |
| 0.78 | 11.57 ± 1.7 | 33 | 0.053 |
| 1.56 | 8.89 ± 1.12 | 48 | 0.016 |
| 3.12 | 5.11 ± 0.27 | 70 | 0.0074 |
| 6.25 | 2.45 ± 0.56 | 86 | 0.0053 |
| 12.5 | 1.07 ± 0.11 | 94 | 0.003 |
| 25 | 0.58 ± 0.05 | 97 | 0.0029 |
| 50 | 0.44 ± 0.12 | 97 | 0.0028 |

As can be seen from the results in Table 2, concentrations as low as 1.56 $\mu$M resveratrol decreased DNA synthesis of keratinocytes significantly. 1.56 $\mu$M resveratrol reduced keratinocyte proliferation by as much as 50%. In both experiments, 50 $\mu$M resveratrol inhibited DNA synthesis completely.

EXAMPLE 3

Example 2 was repeated at various additional concentrations of resveratrol. The results that were obtained are summarized in Table 3.

TABLE 3

EFFECT OF RESVERATROL AT LOW CONCENTRATIONS ON THYMIDINE UPTAKE IN KEPATINOCYTES

| Resveratrol concentration | DNA synthesis (cpm/$\mu$g protein) | % inhibition | P value | Statistically Significant (at p less than 0.5) |
| --- | --- | --- | --- | --- |
| 0.0 $\mu$M | 63.4 ± 5.2 | — | — | — |
| 0.1 $\mu$M | 60.4 ± 4.1 | 5 | 0.502 | NO |
| 0.2 $\mu$M | 56.3 ± 3.0 | 12 | 0.079 | NO |
| 0.3 $\mu$M | 58.8 ± 0.4 | 7 | 0.254 | NO |
| 0.4 $\mu$M | 54.2 ± 1.2 | 14 | 0.051 | NO |
| 0.6 $\mu$M | 59.3 ± 5.5 | 6 | 0.310 | NO |
| 0.8 $\mu$M | 44.4 ± 2.6 | 30 | 0.00013 | YES |
| 1.0 $\mu$M | 37.7 ± 4.0 | 40 | <0.0001 | YES |
| 2.0 $\mu$M | 25.7 ± 2.4 | 59 | <0.0001 | YES |

It can be seen from the results in Table 3 that resveratrol was not effective at reducing keratinocyte proliferation at concentrations lower than 0.8 $\mu$m (or 0.000018 wt. %), including a very low concentration of 0.33 $\mu$m which would be the maximum concentration present in 0.5% grape extract disclosed by JP 6336421.

EXAMPLE 4

This example demonstrates that resveratrol induces differentiation of keratinocytes:

Methodology for Transglutaminase Measurement

During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of N-((-glutamyl) lysine isodipeptide bonds catalyzed by the action of at least two different transglutaminases expressed in the epidermis. Transglutaminase (TG-1) is expressed in abundance in the differentiated layers of the epidermis, especially the granular layer, but is absent in the undifferentiated basal epidermis. Thus, TG-1 is a useful marker of epidermal keratinocyte differentiation with high TG-1 levels indicating a more differentiated state. An ELISA based TG-1 assay, using a TG-1 antibody, was used to assess the state of differentiation of the cultured keratinocytes in the examples that follow.

The level of TG-1 was measured as follows. Keratinocytes were obtained as described in Example 2. For the experiment, about 30,000 cells were plated into each well of 6 well plates and grown for five days, until the cells reach about 20–30% confluence. 2 ml/well of fresh KGM were added daily with 2 $\mu$l of 2–50 mM resveratrol in DMSO for 3 days. Control wells also received 2 $\mu$l of DMSO. After 3 days of treatment, cells were washed twice with PBS and placed in freezer for 2 hours. Cells were then thawed for 2 hours. DNA content of the cells were quantitated by using the DNA binding flurophore, bis-benzimidazole (Hoechst 33258) and measuring the specific fluorescence of the DNA-bound flurophore at 450 nm (excitation at 360 nm).

TG-1 levels of the cells in the wells were determined using the TG-1 specific monoclonal antibody (BC1) (first antibody) (obtained from Amersham Life Sciences) and using a peroxidase labeled rabbit antimouse IgG fragment (second antibody). The plates were blocked by 5% nonfat milk in TBS (Tris buffered saline, 0.01 M Tris, 0.150 M sodium chloride, pH 8.0) for one hour followed by 2 hour incubation with the first antibody (1:4,000 fold dilution) in 1% milk/TBS at room temperature. After rinsing the plates three times with 1% milk/TBS containing 0.05% Tween 20, the plates were incubated with 1:4000 dilution of the second antibody at room temperature for two hours. The plates were rinsed three times with 1% milk/TBS/Tween and three times with TBS. Color was developed by incubation with o-phenylene diamine and hydrogen peroxide. The absorbance was read at 492 nm on a Ultrospec 3000 spectrophotometer (Pharmacia Biotech) and TG-1 levels were calculated as Abs/DNA fluorescence. The mean±standard deviation of at least 3 separate wells were used for calculation and statistical analysis of the data. Values were expressed as absorbance for TG-1 per arbitrary unit of DNA fluorescence of triplicate wells±standard deviation. Results were also expressed as % of control.

The results that were obtained are summarized in Table 4.

TABLE 4

| Resveratrol ($\mu$M) | TG-1 levels/$\mu$g DNA | % of control | p value |
|---|---|---|---|
| EXPERIMENT 1 | | | |
| 0 $\mu$M | 6.74 ± 0.79 | — | — |
| 10 $\mu$M | 8.49 ± 1.77 | 126 | 0.1195 |
| 25 $\mu$M | 10.92 ± 2.29 | 162 | 0.0008 |
| 50 $\mu$M | 22.2 ± 1.50 | 329 | 0.0001 |
| EXPERIMENT 2 | | | |
| 0 $\mu$M | 1.91 ± 0.03 | — | — |
| 2 $\mu$M | 3.42 ± 0.42 | 179 | <0.0001 |
| 5 $\mu$M | 3.51 ± 0.41 | 184 | <0.0001 |
| 10 $\mu$M | 3.61 ± 0.17 | 189 | <0.0001 |
| 25 $\mu$M | 4.69 ± 0.21 | 246 | <0.0001 |
| 50 $\mu$M | 4.65 ± 0.46 | 243 | <0.0001 |

10 $\mu$M resveratrol was not significantly different from control in Experiment 1 due to normal experimental variations in biological systems, but all other concentrations significantly increased transglutaminase expression of keratinocytes, thus proving that resveratrol increases keratinocyte differentiation. In Experiment 2 all concentrations of resveratrol of 2 $\mu$M and higher significantly increased keratinocyte differentiation.

EXAMPLE 5

This example demonstrates that resveratrol inhibits melanin production by skin cells, and thus is a suitable skin lightening active.

B16 F1 cells were purchased from ATCC (Rockville, Md.) Subconfluent B16 cells were seeded in 96 well microtiter plates at a density of 5000 cells/well and cultured overnight in DMEM (Life Technologies, NY) containing 10% Fetal Bovine Serum, 1% penicillin/streptomycin without phenol red) at 37° C. under 5% CO2. After 24 hours, the media was replaced with fresh media containing the treatments. Cells were incubated for 72 hours at which time melanin was visible in the control treatment. Next, the melanin containing media from each well was transferred to a clean 96 well plate and quantified by reading the absorbance at 530 nm using a microplate Spectrophotometer.

In order to ensure that melanin inhibition was not simply due to cell killing, cell viability was assessed by neutral red dye uptake. After the removal of media, 200 $\mu$L of pre-warmed medium containing 25 $\mu$g/ml neutral red dye was added to each well and incubated for 3 hours. Cells were washed 2× with PBS. The dye was extracted by adding 100 L of 50 H2O: 49 ethanol: 1 acetic acid and then gently shaken at room temperature for 20 minutes. The dye was quantified by reading the absorbance at 530 nm. Only viable cells are expected to take up the dye and the absorbance is directly proportional to the number of viable cells surviving the treatment.

For each treatment, the average of four replicate readings was calculated and expressed as percent of the average for the untreated control. Statistical significance was determined using the student's t-test (reported only for the treatments that showed greater than 50% viability).

The results that were obtained are summarized in Table 5. The lower the % melanin value (with a viability value of >50%), the better the skin lightening potential.

TABLE 5

| Sample | % Melanin | % Viability |
|---|---|---|
| Control | 100 | 100 |
| Resveratrol 10 $\mu$M | 80* | 94.6 |
| Resveratrol 25 $\mu$M | 4.0* | 86.8 |
| Resveratrol 50 $\mu$M | 3.9* | 69.2 |
| Resveratrol 100 $\mu$M | 6.6 | 1.8 |

It can be seen from the results in Table 5 that resveratrol inhibited melanin production by skin cells at all concentrations tested, where viability was greater than 50%.

EXAMPLE 6

This example demonstrates that resveratrol alleviates skin inflammation that may be caused by alpha-hydroxy acids.

Resveratrol is a known cyclo-oxygenase inhibitor. Inhibition of cyclooxygenase reduces the conversion of arachidonic acid to pro-inflammatory substances such as prostaglandins, including PGE2. While inhibition of cyclooxygenase would be expected to reduce inflammation, not all cyclooxygenase inhibitors reduce irritation potentially associated with a cosmetic ingredient such as alpha hydroxy acids.

EXAMPLE 6A

Irritation Test Method

Four Exposure Patch Test: The objective was to compare the level of irritation produced by various test materials after repeated patch applications. The test materials were held in contact with the skin under occlusive conditions. The outer upper arm of the panelist was designated as thea rea of application. Bandage type dressing (Scanpor tape) was used to hold the patches (25 mm Hill Top Chamber fitted with 18 mm diameter disc of Webril padding) into place. Both upper arms of the panelist were used. Patches were applied in a balanced random order.

Patches were applied at 9:00 o'clock Monday morning and removed at 9:00 o'clock Tuesday morning (24 hour exposure). A new set of patches was applied at 3:00 o'clock Tuesday afternoon and removed Wednesday morning at 9:00 o'clock (18 hour exposure). A third set of patches was applied at 3:00 o'clock Wednesday afternoon and removed Thursday morning at 9:00 o'clock (18 hour exposure). A final set of patches was applied at 3:00 o'clock Thursday afternoon and removed Friday morning at 9:00 o'clock (18 hour exposure).

Each time the patches were removed, the sites were rinsed with warm water and patted dry. The test sites were then marked with a surgical skin marking pen to ensure location for grading and subsequent patch applications. Test sites were evaluated at 3:00 p.m. on Tuesday, Wednesday, Thursday, and Friday of the study, prior to re-patching.

Skin irritation such as moderate redness, dryness, and/or itching of the test site is expected. Swelling of the test sites was possible. If any test site had moderate redness or any swelling at any evaluation, that particular test site was not repatched.

The test sites on each arm were visually ranked by two trained examiners under consistent lighting. The test sites were ranked in order of severity. The examiner ranking responses at the first evaluation period continued ranking the sites each day throughout the study.

In ranking the reactions, the site with the most severe response was given the lowest score. The site with the second most severe response was given the second lowest score, etc. There was no forced ranking. If two or more sites had no response or the same response (no difference between sites), an average of the ranks was assigned. If a site had been discontinued, due to degree of irritation, the site retained the rank it received at the time dosing was discontinued.

Statistical Analysis

The ranking results from the patch treatments were statistically compared by nonparametric statistical methods. The test materials containing the anti-irritants were compared to the corresponding control containing only hydroxy acid, using Friedman's Rank Sum at each evaluation point with the panelist acting as a block (i.e., each panelist was tested with each test treatment). A p-value of less than 0.10 was considered to indicate statistical significance.

Compositions containing ingredients as indicated in Table 6A, were tested using the Irritation Test Method. Twenty (20) subjects were tested. The results that were obtained are summarized in Table 6A. The higher the sum of ranks, the less is the irritation.

| BASE FORMULA | | |
|---|---|---|
| FULL CHEMICAL NAME OR CFTA NAME | TRADE NAME AND % ACTIVE | WT. % |
| water, DI | | 46.54 |
| disodium EDTA | Sequesterene Na2 | 0.05 |
| magnesium aluminum silicate | Veegum Ultra | 0.6 |
| methyl paraben | Methyl Paraben | 0.15 |
| simethicone | DC Antifoam Emulsion | 0.01 |
| butylene glycol 1,3 | Butylene Glycol 1,3 | 3.0 |
| hydroxyethylcellulose | Natrosol 250 HHR | 0.5 |
| glycerine, USP | Glycerine USP | 2.0 |
| xanthan gum | Keltrol 1000 | 0.2 |
| triethanolamine | Triethanolamine 99 (%) | 1.2 |
| stearic acid | Pristerene 4911 | 3.0 |
| propyl paraben NF | Propylparaben NF | 0.1 |
| glyceryl hydrostearate | Naturechem GMHS | 1.5 |
| stearyl alcohol | Lanette 18 DEO | 1.5 |
| isostearyl palmitate | Protachem ISP | 6.0 |
| C12-15 alcohols octanoate | Hetester FAO | 3.0 |
| dimethicone | Silicone Fluid 200 (50 cts) | 1.0 |
| cholesterol NF | Cholesterol NF | 0.5 |
| sorbitan stearate | Sorbitan Stearate | 1.0 |
| butylated hydroxytoluene | Embanox BHT | 0.05 |
| tocopheryl acetate | Vitamin E Acetate | 0.1 |
| PEG-100 stearate | MYRJ 59 | 2.0 |
| sodium stearoyl lactylate | Pationic SSL | 0.5 |
| retinyl palmitate | Vit. A Palmitate 84% | 0.06 |
| hydroxy caprylic acid | Hydroxy caprylic acid | 0.1 |
| water, DI | | q.s. to 99.80 |

-continued

| BASE FORMULA | | |
|---|---|---|
| FULL CHEMICAL NAME OR CFTA NAME | TRADE NAME AND % ACTIVE | WT. % |
| alpha-bisabolol | Alpha-bisabolol | 0.2 |
| pH | | 7–8 |

TABLE 6A

| COMPOSITION | INGREDIENTS | SUM OF RANKS (Day 1) | SUM OF RANKS (Day 4) |
|---|---|---|---|
| 1 | Base Formula | 65.5 | 79.5 |
| 2 | Base Formula + 8% Glycolic acid | 63 | 72 |
| 3 | Composition #2 + 0.1% resveratrol | 85[a] | 66 |

[a]significantly less irritating than composition 2.

It can be seen from the results in Table 6A that resveratrol (Composition 3) significantly reduced the irritation induced by composition #2 (containing 8% glycolic acid) on Day 1, after the initial exposure to composition #2.

Comparative Example 6B

Compositions containing ingredients as indicated in Table 6B, were tested using the Irritation Test Method described in Example 6A. Twenty-two (22) subjects were tested. The results that were obtained are summarized in Table 6B. The higher the sum of ranks, the less is the irritation.

TABLE 6B

| COMPOSITION | INGREDIENTS | SUM OF RANKS (Day 1) | SUM OF RANKS (Day 4) |
|---|---|---|---|
| 1 | Base Formula | 81 | 90.5 |
| 2 | Base Fomnula + 8% Glycolic acid | 75 | 73.5 |
| 4 | Composition #2 + 5% Ibuprofen | 71.5 | 65.5 |

It can be seen from the results in Table 6B, that ibuprofen, a known anti-inflammatory ingredient (composition #4) did not reduce the irritation of the Formula which contains 8% glycolic acid (composition #2).

Comparative Example 6C

Compositions containing ingredients as indicated in Table 6C, were tested using the Irritation Test Method, as described in Example 6A. Nineteen (19) subjects were tested. The results that were obtained are summarized in Table 6C. The higher the sum of ranks ranks, the less is the irritation.

TABLE 6C

| COMPOSITION | INGREDIENTS | SUM OF RANKS (Day 1) | SUM OF RANKS (Day 4) |
|---|---|---|---|
| 2 | Base Formula + 8% Glycolic acid | 70 | 62 |

TABLE 6C-continued

| COMPOSITION | INGREDIENTS | SUM OF RANKS (Day 1) | SUM OF RANKS (Day 4) |
|---|---|---|---|
| 5 | Composition #2 + 1% Indomethacin | 53.5 | 52.5 |

It can be seen from the results in Table 6C, that indomethacin, a known cyclo-oxygenase inhibitor and anti-inflammatory ingredient (composition #5) did not reduce the irritation of the Formula which contains 8% glycolic acid (composition #2).

Examples 7–12 illustrate skin care compositions according to the present invention. The compositions can be processed in conventional manner. They are suitable for cosmetic use. In particular, the compositions are suitable for application to wrinkled, lined, rough, dry, flaky, aged and/or UV-damaged skin to improve the appearance and the feel thereof as well as for application to healthy skin to prevent or retard deterioration thereof. The composition are also particularly suitable to lighten the skin and/or to reduce the irritation, sting, or inflammation that may be associated with the use of alpha-hydroxy acids.

EXAMPLE 7

This example illustrates a high internal phase water-in-oil emulsion incorporating the inventive composition.

| | % w/w |
|---|---|
| RESVERATROL | 0.5 |
| 1,3-dimethyl-2-imidazolidinone | 0.2 |
| Brij 92* | 5 |
| Bentone 38 | 0.5 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 8

This example illustrates an oil-in-water cream incorporating the inventive composition.

| | % w/w |
|---|---|
| RESVERATROL | 2 |
| Glycolic Acid | 8 |
| Mineral oil | 4 |
| 1,3-dimethyl-2-imidazolidinone | 1 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 9

This example illustrates an alcoholic lotion incorporating the composition according to the invention.

| | % w.w |
|---|---|
| RESVERATROL | 5 |
| 1,3-dimethyl-2-imidazolidinone | 0.1 |
| Ethanol | 40 |
| Perfume | qs |
| Butylated hydroxy toluene | 0.01 |
| Water | to 100 |

EXAMPLE 10

This example illustrates another alcoholic lotion containing the inventive composition.

| | % w/w |
|---|---|
| RESVERATROL | 10 |
| 1,3-dimethyl-2-imidazolidinone | 0.01 |
| Ethanol | 40 |
| Antioxidant | 0.1 |
| Perfume | qs |
| Water | to 100 |

EXAMPLE 11

This example illustrates a suncare cream incorporating the composition of the invention:

| | % w/w |
|---|---|
| RESVERATROL | 2 |
| 1,3-dimethyl-2 imidazolidinone | 0.2 |
| Silicone oil 200 cts | 7.5 |
| Glycerylmonostearate | 3 |
| Cetosteryl alcohol | 1.6 |
| polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 12

This example illustrates a non-aqueous skin care composition incorporating the inventive combination.

| | % w/w |
|---|---|
| RESVERATROL | 5 |
| 1,3-dimethyl-2-imidazolidinone | 1 |
| Silicone gum SE-30[1] | 10 |
| Silicone fluid 345[2] | 20 |
| Silicone fluid 344[3] | 50.26 |
| Squalene | 10 |
| Linoleic acid | 0.01 |
| Cholesterol | 0.03 |
| 2-hydroxy-n-octanoic acid | 0.7 |

-continued

This example illustrates a non-aqueous skin care composition incorporating the inventive combination.

| | % w/w |
|---|---|
| Vitamin E linoleate | 0.5 |
| Herbal oil | 0.5 |
| Ethanol | 2 |

[1] A dimethyl silicone polymer having a molecular weight of least 50,000 and a viscosity of at least 10,000 centistokes at 25° C., available from GEC
[2] Dimethyl siloxane cyclic pentamer, available from Dow Corning Corp.
[3] Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic method of controlling skin irritations, sting or inflammation caused by alpha hydroxy acid, the method comprising applying to the skin the composition comprising:

(a) resveratrol in an amount of from 0.00002 to 10 wt. %;
(b) hydroxy acid in an amount of from about 0.01% to about 20%; and
(c) a cosmetically acceptable vehicle.

* * * * *